United States Patent [19]
Jacobs

[11] Patent Number: 5,405,312
[45] Date of Patent: Apr. 11, 1995

[54] CUSTOM FIT BODY GUARDS

[75] Inventor: Scott Jacobs, Denver, Colo.

[73] Assignee: Safe-T-Gard Corporation, Lakewood, Colo.

[21] Appl. No.: 902,061

[22] Filed: Jun. 22, 1992

[51] Int. Cl.⁶ .................... A61F 5/00; A61F 13/00
[52] U.S. Cl. ................................ 602/5; 602/7; 128/892
[58] Field of Search ............ 602/23, 24, 5–8; 128/892; 2/2, 16, 22, 24, 44, 45, 19, 23; 273/25

[56] References Cited

U.S. PATENT DOCUMENTS

| | | |
|---|---|---|
| 2,495,119 | 1/1950 | McDevitt . |
| 2,800,129 | 7/1957 | Van Swaay . |
| 2,834,341 | 5/1958 | Stryker ................... 602/23 |
| 2,917,774 | 12/1959 | Archer . |
| 3,089,486 | 5/1963 | Pike . |
| 3,312,218 | 4/1967 | Jacobs . |
| 3,322,873 | 5/1967 | Hitchcock . |
| 3,446,880 | 5/1969 | Enicks . |
| 3,911,497 | 10/1975 | Lewis ..................... 128/881 |
| 4,136,686 | 1/1979 | Arluck ..................... 602/7 |
| 4,292,263 | 9/1981 | Hanrahan . |
| 4,320,748 | 3/1982 | Racette ..................... 602/23 |
| 4,349,016 | 9/1982 | Glassman ................. 602/23 |
| 4,393,866 | 7/1983 | Finnieston ............... 602/23 |
| 4,457,308 | 7/1984 | Golke . |
| 4,483,333 | 11/1984 | Wartmen ................. 602/7 |
| 4,527,565 | 7/1985 | Ellis . |
| 4,527,566 | 7/1985 | Abare . |
| 4,559,047 | 12/1985 | Kapralis . |
| 4,641,639 | 2/1987 | Padilla ..................... 602/23 |
| 4,947,838 | 8/1990 | Giannetti ................. 602/23 |
| 4,964,402 | 10/1990 | Grim . |
| 4,972,832 | 11/1990 | Trapini . |
| 4,981,132 | 1/1991 | Chong ..................... 602/23 |
| 5,000,169 | 3/1991 | Swicegood ............... 602/23 |
| 5,035,241 | 7/1991 | Walasek . |
| 5,056,158 | 10/1991 | Lutz ........................ 2/22 |
| 5,065,457 | 11/1991 | Henson ................... 2/22 |
| 5,074,292 | 12/1991 | Cox ......................... 602/7 |
| 5,195,944 | 3/1993 | Schlogel ................. 602/21 |
| 5,259,831 | 11/1993 | LeBron ................... 602/7 |

OTHER PUBLICATIONS

"Advertising Letter and Instructions", (No Date) Sports Medical Aids Co. of Cronulla, Australia.

Primary Examiner—Michael A. Brown
Attorney, Agent, or Firm—James E. Pittenger

[57] ABSTRACT

A custom fit body part guard or shield is disclosed which includes a thin shell formed from an ionomer resin which has a softening temperature within the range of 60°–80° C. The shell material of approximately 1–6 millimeters thickness is partially molded to fit the area of the body where the device is intended to be used. A layer of perforated foam material can be adhered to the inside surface of the guard to further protect the user's skin and absorb or distribute impact energy during use. By holding the guard under ordinary hot tap water it can be softened to a moldable consistency. By firmly applying and holding the guard on the surface of the area of the body where it is intended to be used and allowing the guard to cool to ambient temperature the guard will take a permanent set to a custom shape which follows the exact shape and contour of the body part. The device can be arranged to protect passive areas of the body, such as the shin or forearms or can be used to protect body joints, such as elbows or knees.

13 Claims, 3 Drawing Sheets

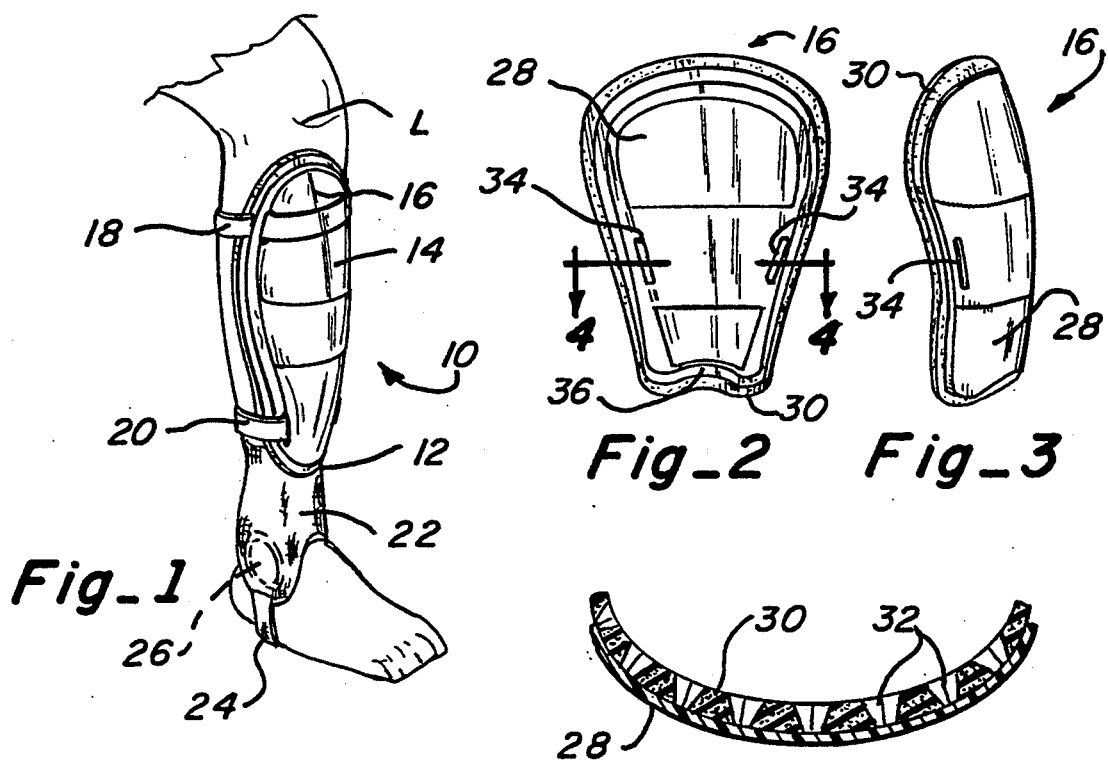
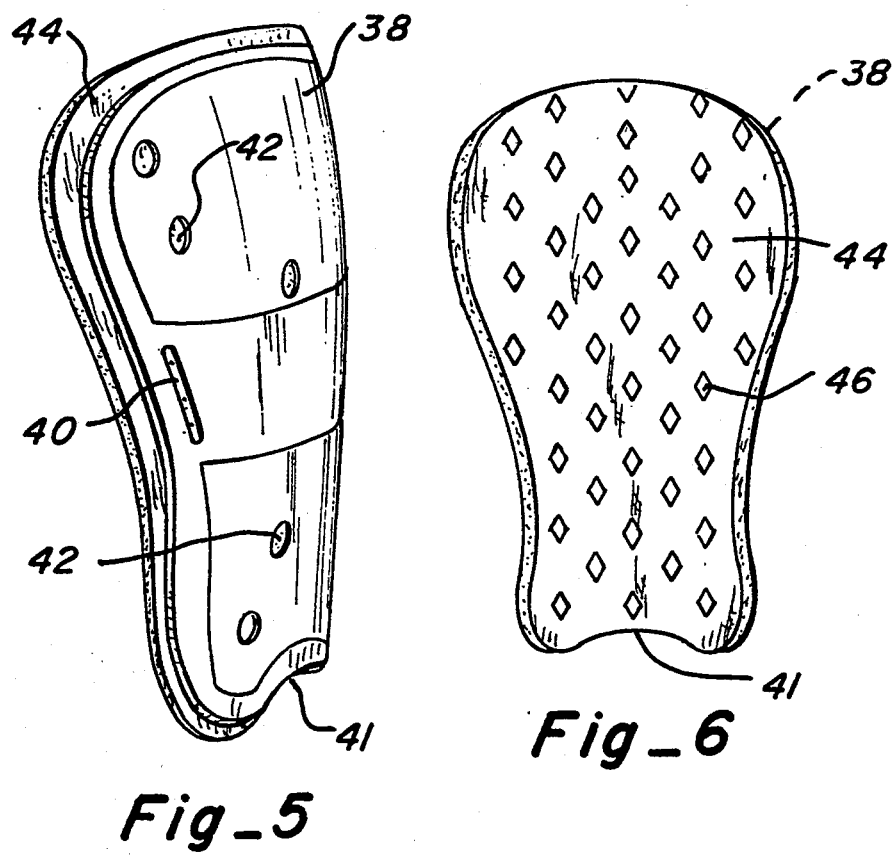

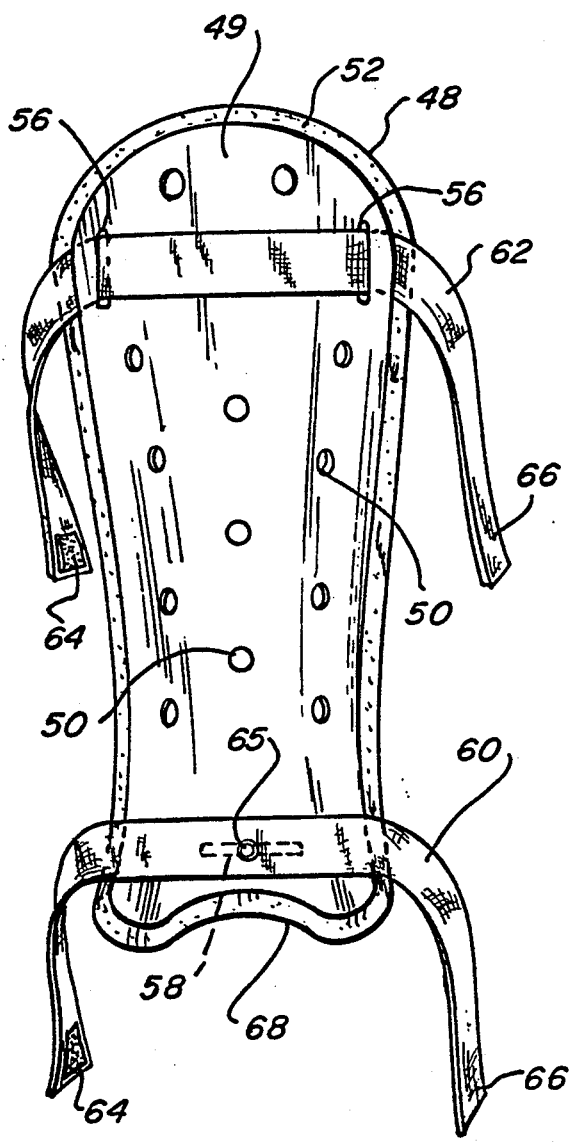
Fig_7
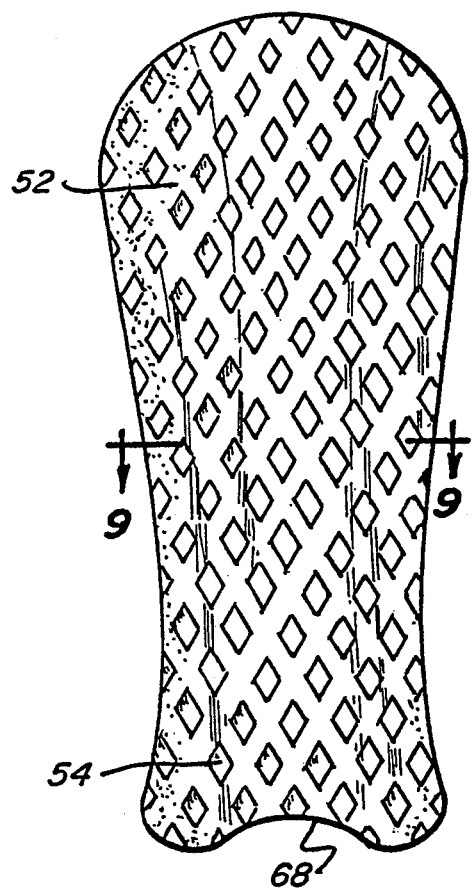
Fig_8
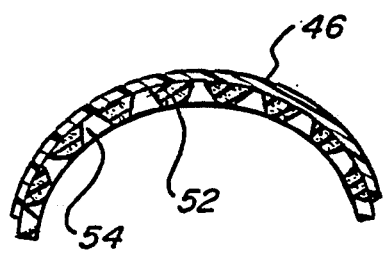
Fig_9

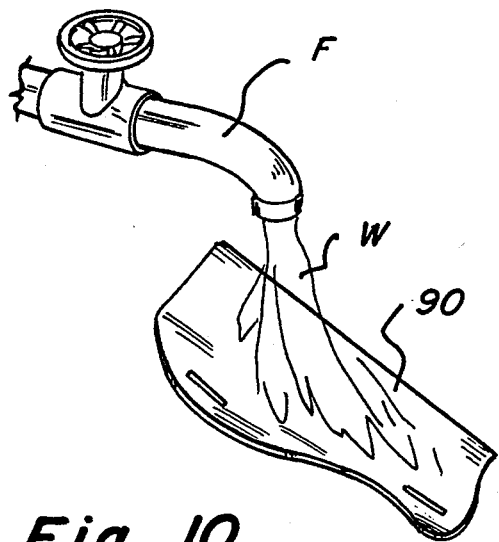
Fig_10
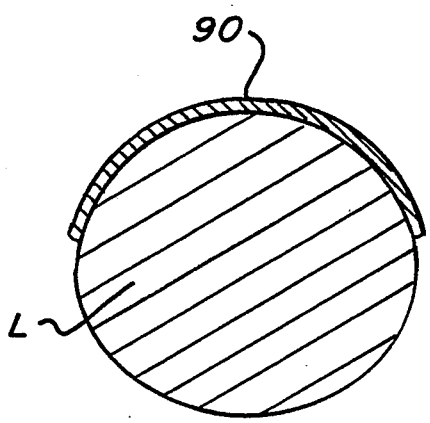
Fig_12
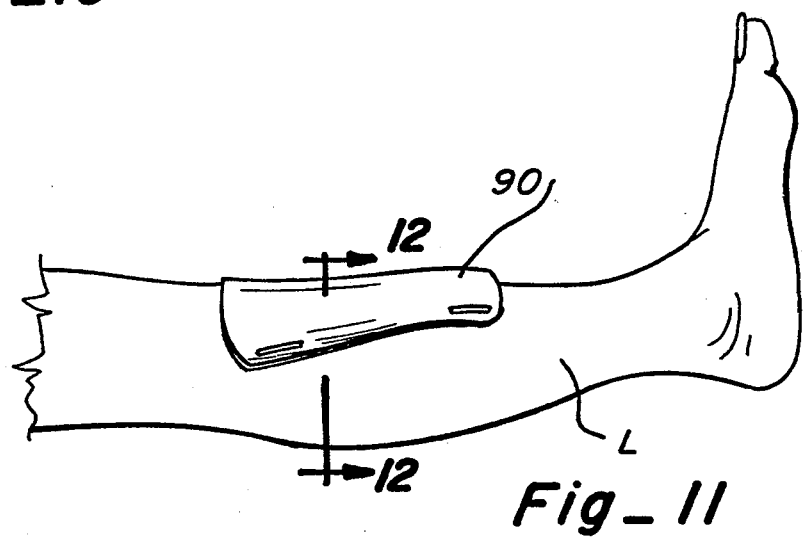
Fig_11
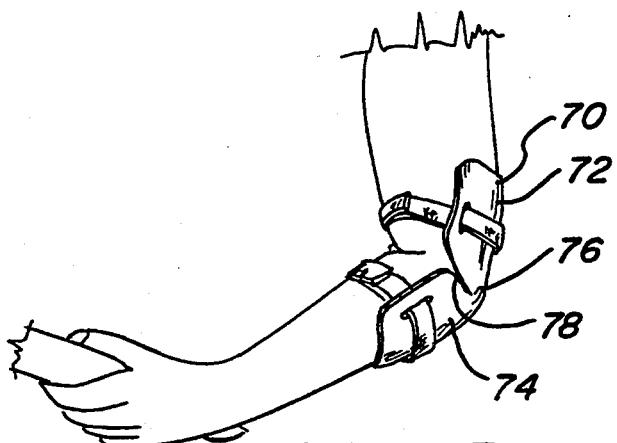
Fig_13
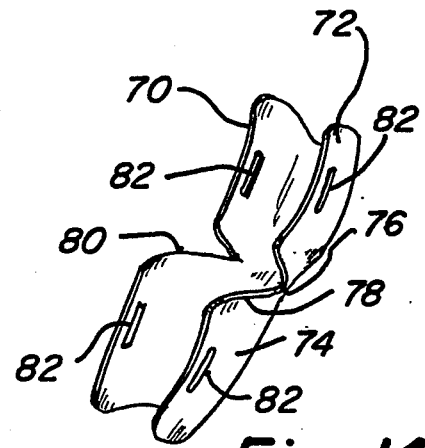
Fig_14

CUSTOM FIT BODY GUARDS

FIELD OF THE INVENTION

This invention is directed to a guard for a user's body which can be custom fitted. It is more specifically directed to a guard for protecting a body part of a user, wherein the guard can be heated to a relatively low temperature and molded to custom fit the corresponding body part.

BACKGROUND OF THE INVENTION

In the past it has been common practice to use various types of hard and rigid metal or plastic materials to fabricate shields or guards which can be used to protect an individual during sporting events or other types of strenuous activity. In many cases, a hard and rigid shell which fits the overall general contour of that part of the body which is intended to be protected is combined in conjunction with a pad, usually of a soft cloth or foam material, which cushions the shell from contact with the user's body. Thus, an impact or blow to this protected part of the body allows the impact or energy of the blow to be distributed over a broader area allowing the body to absorb the energy without injury or damage.

One of the biggest problems with the conventional guards or shields which have been used in the past is the fact that these shields do not generally fit the specific part of the body that is intended to be protected. Most shields are sized and shaped to fit the average person and as we well know there is no average person. Every individual is different and it is common knowledge that there is a difference between even the legs, arms and other areas of some individuals. As a result, the shields that have been used to date have been found to be inadequate and fail to fully protect the user's body. This is to say that even though they have performed an adequate function up to this point the present guards or shields still allow a number of injuries, primarily because the guards or shields do not properly fit the user and thus do not properly couple and dissipate the impact energy that is applied to the guard.

In the past, various types of moldable materials have been used to mold an individual product to the individual user. This type of approach to the problem has been primarily applied in mouth guards which are used for many athletic events and also for orthopedic appliances, such as splints and braces.

With respect to the orthopedic devices, usually a foam pad is applied to the underside of the splint in order to render the device more comfortable when the device is used for a long term without removal. In many cases with orthopedic devices the material that is used is quite rigid to prevent any flexure or movement in the body part or joint over which the splint is applied. Thus, the materials that have been used dictate the methods of applying temperature in order to soften the material so that it can be formed. One of these materials is "Plexiglass" which requires a temperature of approximately 149° C. (300° F.) in order to allow the material to be pliable enough to be formed. Naturally a temperature of this magnitude is quite difficult to handle and is unsafe when heated. This material presents problems in applying the heat as well as possibly burning or injuring the patient when the device is shaped.

The plastic mouth guard products which have been in use for a number of years have been fabricated from materials which are far softer and more pliable then those used in pads, shields or guards used to protect participants in sport contests. As a result of the pliability of the particular materials used and the fact that the material is used in the mouth, the problems which exist in the manufacture and use of the mouth piece guard are quite different than those encountered in body guard products. It is acknowledged that the material used in a mouth protector is of the mid-temperature type which can be softened and molded by immersion in boiling water. One of the major differences is that the mouth protector is used within the body and thus is maintained at a relatively constant body temperature of approximately 38° C. (98°–100° F.). As a result, the material must set and retain its shape at higher temperatures than those required for normal ambient temperature use. In addition, the material that is used must have stringent specification requirements which relate to body compatibility.

The problems encountered with these products are considerably different than those which are encountered in the attempt to shape or fit an external guard or shield to the outside surface of the user's body in order to more completely protect the user from injury.

INFORMATION DISCLOSURE STATEMENT

The following information is provided in compliance with the inventor's duty to disclose all pertinent information which is relevant to the examination of the subject application. The listed patents are known to the applicant and are believed to be pertinent. It is not to be assumed that this list is all inclusive of any search which may have been performed for or by the applicant. In addition, it is possible that other patents may have been considered by the applicant but only those items which are listed are believed to be pertinent and are of concern with respect to the examination of this application.

The Van Swaay patent (U.S. Pat No. 2,800,129) is a method of forming a splint or orthopedic device in which the thermoplastic material of the splint is subjected to a relatively high temperature in order to plasticize and shape the material. A foam pad is provided on the inside surface of the splint in order to form a heat insulator to protect the patient's skin during the forming process. This patent discloses the use of a material, such as "Plexiglas" which is relatively thick and heavy which would render it unsuitable for use as an athletic guard or shield.

The Jacobs patent (U.S. Pat. No. 3,312,218) discloses a moldable mouth guard manufactured from a relatively flexible soft plastic material which can be heated in boiling water to a softening temperature and manually inserted into the mouth to be formed or molded to the user's teeth. The materials which are used in a mouth protector of this type are not acceptable for use in fabricating the guards or shields which can be used on the outside surfaces of the user's body. In addition the molding process of the present invention is considerably different then that which is disclosed in this patent.

The Hitchcock patent (U.S. Pat. No. 3,322,873) shows a resilient custom-fit body protector. This disclosure shows a garment which is made of cloth or fabric like material which is positioned over the part of the body which is to be protected. A semi-liquid composition is then plastered or layered over the outside surface of the garment where protection is required and this material is then dried or set to a semi-rigid or resilient consistency. The mixture can be applied in one or more layers. There is no teaching in this patent of using a heat application for softening, molding or curing the material.

The Enicks patent (U.S. Pat. No. 3,446,880) shows a method of manufacturing protective pads for athletic or sports use. The pads are fabricated from a foam plastic material which has an outer skin. These pads are partially formed in the shape required for their intended use. Because the pads are quite resilient they can be taped or held by straps to the desired area of the user's body. There is no teaching in this patent of permanently molding or shaping the device to the actual user. These pads are only preshaped and have enough flexibility to be held to the contour of the user's body.

The McDevitt patent (U.S. Pat. No. 2,495,119) and Archer patent (U.S. Pat. No. 2,917,774) disclose the use of a molding process for fabricating objects that closely fit various parts of the body. The Archer patent discloses the use of a mold to form a custom fit temple for glasses. The McDevitt patent shows a mold which is used to form a custom fit grip for golf clubs. In each case the mold is filled with a suitable plastic material which sets to form the custom fit object.

The Pike patent (U.S. Pat. No. 3,089,486) shows a flexible bandage that is impregnated with a controllable setting polymer compound. The bandage is wrapped around the injured part of the user's body and a controlled chemical reaction takes place to fuse and set the material into a rigid cast. The polymerization can be accelerated by applying heat to the applied bandage. This arrangement does not disclose a semi-shaped guard or shield which is softened by the application of heat to custom fit it to the user's body as described in the present invention.

The Golke, et al patent (U.S. Pat. No. 4,457,308), Abere patent (U.S. Pat. No. 4,527,566), Grim, et al patent (U.S. Pat. No. 4,964,402), Trapini, et al patent (U.S. Pat. No. 4,972,832), Ellis patent (U.S. Pat. No. 4,527,565) and Kapralis, et al patent (U.S. Pat. No. 4,559,047) all teach the use of various types of body covering articles which have some form of pad or material which can be either heated or cooled which can be used to medically treat or heal various parts of the user's body. Although these devices generally mold or shape to the contour of the user's body, they are not intended to produce a permanent guard or shield for protecting the user's body against injury. Although these devices temporarily contour or fit close to the body part it is only a temporary application.

The Walasek, et al patent (U.S. Pat. No. 5,035,241) shows a reusable heat insulated compress which is applied and held in close proximity to an area of the user's body. This device is inserted into a microwave oven whereby the internal gel is physically changed by the addition of heat so that the heat can be transferred to the user's body.

The Hanrahan, et al patent (U.S. Pat. No. 4,292,263) discloses a foam plastic pad which is integrally molded to a fabric. These pads can be partially formed for the average athlete and can be molded directly to the uniform to be worn by the user.

SUMMARY OF THE INVENTION

A guard, pad or shield is provided for use in athletic contests to protect various parts of the user's body from impact or possible injury during various athletic or sporting activities.

For the sake of illustration throughout this application, the device will be referred to as a "guard". This term is intended to be used to identify all possible devices which can be used for protection, such as guards, pads, shields, cups or any other protector which can be used to protect the user's body against impact and possible injury or damage.

In this invention the body guard is composed of a shell and possible a holding device and layer of padding material. The shell is fabricated from a relatively thin, hard material, but one that is relatively flexible at normal atmospheric temperatures. In this way, the shell material will flex with the body part or joint during actual use of the product. The shell is originally manufactured in a flat or partially formed configuration and when the user actually purchases the guard he or she can then custom fit the final shape of the shell to the individual body part where the guard is intended to be used.

It is to be understood that the guard which is the subject of this invention can be used either on a passive part of the body, such as the shin, forearm, thigh, rib cage, groin, hip or face. At the same time, it is also possible to fabricate the device according to the present invention for protection of the elbow, knee or shoulder joint of the wearer. In this way, the ends of the guard can be secured to the portion of the body adjacent the joint with the center portion of the guard which is sufficiently flexible arranged to pass around or cover the actual movable joint.

It has been found that a certain type of plastic, such as ethylene/methacrylic acid based copolymers. This material includes the ionomer resins. The ionomer resins are thermal plastic polymers that are "ionically cross-linked". The ionomer resin which has been found to be quite satisfactory for this purpose is manufactured by Dupont and sold under the trademark "Surlyn". "Surlyn" is commonly used in the cover for golf balls. Many of the characteristics which are associated with the Olefin polymers are evident in the ionomer resins. This resin material can be easily molded and shaped similar to the processes which are used for low density polyethylene or ethylene vinylacetate copolymers. It has been found that the Surlyn 9910 and 8870 ionomer resins have characteristics which are quite satisfactory for use in the manufacture of a guard according to the present invention.

It is also understood that other ionomers manufactured by various companies but having similar physical characteristics can be used for manufacturing the guards according to the present invention.

There are several characteristics of the ionomer resins, which are quite desirable for this use. One of these is the fact that the material has low temperature impact toughness as well as abrasion resistance. In addition, the material can be formed and molded at a relatively low temperature within the temperature range of approximately 60°-66° C. (140°-150° F.). Although higher temperatures may make the material more pliable, they are not required and the desired temperatures can be quite easily obtained through the common domestic hot water tap or faucet.

To provide additional comfort and protection to the skin of the user, a plastic foam padding material which can have a thickness of approximately 3-9 mm ($\frac{1}{8}$-$\frac{3}{8}$") can be adhered to the surface of the shell which would normally be in contact with the skin of the user. This foam material can be unperforated or perforated and it is found that material which has a waffle type perforation pattern having 3-5 mm (⅛-3/16") openings can be quite satisfactory. The foam material is also helpful when the device is custom fitted to the user. The foam material insulates the skin of the user from the heated, material of the shell.

The custom fitting of the guard to a portion of the user's body is a simple process of holding the shell portion of the guard under running hot water which can be obtained from a domestic hot water faucet. After about 30-90 seconds the material will become quite pliable and can be applied directly to the user's body with the foam plastic surface protecting the user or the guard can be inserted into a guard holder or receptacle that is worn during use. The guard is held tightly against the intended body part so that it closely conforms to the contours of that area. The shell material as it cools to room temperature will set and recover it's rigidity and permanently retain the final shape. In this way, the user has a custom fitted guard which closely fits the contours of the intended area of use and thus, greatly improves the protection which can be provided. It is also to be understood that the shell can be removed from the body after it has been shaped and allowed to air cool or it can be submerged in ice water.

The other major benefit of the present invention is that it is extremely simple and inexpensive to manufacture and at the same time the actual device is quite lightweight and comfortable to wear. This feature is of great importance in athletic contests, such as football, hockey, soccer, lacrosse or cricket. In addition, a protective device according to the present invention can be used for protection in dangerous activities, such as skate boarding or skating with in-line skates. Wherever there is a high degree of risk from falling or impacting stationary objects or other individuals, a guard according to the present invention can be of considerable value.

BRIEF DESCRIPTION OF THE DRAWINGS

FIG. 1 is an isometric view showing the leg of an athlete protected by a shin guard fabricated in accordance with the present invention;

FIG. 2 is a front view of a guard according to the present invention;

FIG. 3 is a side view of the guard seen in FIG. 2;

FIG. 4 is a cross-sectional view taken along lines 4—4 of FIG. 2;

FIG. 5 is an isometric view of another embodiment of the guard according to the present invention;

FIG. 6 is a rear view showing a perforated foam pad adhered to the rear surface of the guard;

FIG. 7 is a front view of another embodiment of the guard showing straps for holding the guard in place;

FIG. 8 is a rear view of the guard shown in FIG. 7;

FIG. 9 is a cross-sectional view taken along the lines 9—9 of FIG. 8;

FIG. 10 is a pictorial view showing the guard being heated by use of hot water;

FIG. 11 is a pictorial view showing the leg of the user with the heated guard applied to the shin;

FIG. 12 is a cross-sectional view taken along the lines 12—12 of FIG. 11 and shows the guard held in close proximity to the outer surface of the leg in order to custom fit it to the user's body;

FIG. 13 is another embodiment of the present invention showing a custom fit guard for protecting the elbow area; and FIG. 14 is a perspective view of the guard shown in FIG. 13 with a linking section for protecting the user's pivotal joint area.

DETAILED DESCRIPTION OF THE INVENTION

Turning now more specifically to the drawings, FIG. 1 shows a guard or protective shield 10 which is mounted or attached to the shin or front of the user's leg (L). The guard 10 as illustrated herein includes a padded support sleeve 12 having a front pocket 14 and a molded guard 16 inserted in the front pocket 14. Straps or bands 18, 20 can be used to attach the padded support sleeve to the leg (L) of the user. The straps or bands 18, 20 usually have their ends adjustably held together with hook and loop material, such as Velcro or they can be a continuous elastic loop. A downward extension 22 can be provided for the padded support sleeve 12 which will envelope both sides of the ankle area of the user and can have a foot strap 24 to hold the padded sleeve in proper position.

The extension 22 can be of a padded or foam material which can be surrounded with a cloth or textile material suitable for padding and protecting the ankle and foot. Molded disks formed from a relatively hard resilient material can be permanently inserted on each side of the extension 22 to form an ankle guard 24 on each side of the foot.

The guard 16 is molded and preshaped to generally fit the shin or body part of most users. The guard 16 can be firmly inserted into the pocket 14 provided in the padded support sleeve 12 to hold it in proper position during use to provide the required protection to the body part, such as the shinbone area of the leg (L). The guard 16 forms a very important element and the basis for the applicant's invention. Although the guard 16 is shown as being held in position in the pocket 14 of the padded support sleeve 12, it is also possible that the guard 16 can be inserted into a long knee sock which can be worn by the user. Although this arrangement is not as secure in positioning and holding the guard in place, this is a common practice by many soccer players and is quite satisfactory for the present invention.

A guard 16 which is suitable for shin protection is shown in FIGS. 2-4. In this preferred embodiment, the guard 16 is formed from a thin, hard outer shell 28 which can be preformed from thin sheet material or it can be injection molded. A suitable foam padding material 30 is permanently adhered to the back surface of the shell 28 to provide additional protection and comfort. The foam padding material 30 can have a plurality of random or symmetrically patterned holes or apertures 32 formed therein to allow ventilation and to spread and distribute energy upon impact on the surface of the shell 28. As will be explained later the thickness of the shell 28 can be approximately 1-6 mm in thickness while the foam padding material is approximately 3-9 mm in thickness. These dimensions have been found to be quite satisfactory for protection when using the guard as described in this application.

Any number of ways can be used to mount the guard 16 on the user's body to provide the desired impact and injury protection. As shown in FIG. 2, slots 34 can be provided on each side of the shell 28 to allow the insertion of a suitable strap (not shown) which could be used to hold the guard 16 in place. A curved portion 36 having a concave upwardly extending cutout can be provided to provide clearance and eliminate interference with movement of the foot.

The foam padding material 30 can be permanently attached to the inner surface of the shell 28 by any suitable arrangement, such as, by the use of contact cement, epoxies or any other adhesive, usually waterproof, which will suitably attach the foam material 30 to the shell 28 to prevent its release or removal. It is desired that once the foam material 30 is positioned on the shell 28 it will remain there to provide the necessary energy absorption and protection. It is also understood that in use with the padded support sleeve 12 as shown in FIG. 1, it is possible that the shell 28 can be used without the foam material 30 and be inserted by itself in the padded sleeve 12. In this arrangement the insulation or foam material provided in the padded support sleeve 12 will take the place of the padding material 30 that can be permanently attached to the shell 28.

In another embodiment of the guard 16 as shown in FIGS. 5 and 6, a larger and more elongated shell 38 is shown which has slots 40 and ventilation apertures 42. Foam padding material 44 is cut to leave an excess margin around the outside perimeter of the shell 38 and is permanently attached with suitable adhesive to the back surface of the shell 38. Holes or apertures 46 can be provided in a random or symmetrical pattern in the foam padding material 44. It is desirable to use a high density padding material 44 to assist the material of the shell 38 to absorb the impact energy that can be received by the user and to properly protect and distribute this energy to the surface and bone structure of the user's body. The primary difference in this embodiment is the elongated size of the material of the shell 38 and its use to cover the majority of the frontal area of the leg to adequately protect the shinbone of the user. A suitable elastic band or a strap having Velcro or other attaching means can be threaded through the slots 40 provided on each side of the shell 38. It is also possible that additional slots can be provided at the upper and lower areas of the shell 38 to provide a dual strap attachment.

The guard embodiment as shown in FIG. 7-9 shows another arrangement which can be provided in which the guard 48 is of an elongated narrow configuration to lie on the frontal bone portion of the user's leg to provide a lighter weight configuration. The shell 49 can have ventilation holes 50 which can be formed in a sequence or random pattern throughout the surface of the shell 49. It is important not to have an excess number of ventilation holes 50 which would possibly deteriorate the overall structural strength of the shell 49. It is suitable, however, to provide the necessary number of holes to allow the guard to be used without retaining excess heat adjacent to the user's skin which could cause discomfort and irritation. Again, padding material 52 having outer dimensions which provide a narrow margin around the outside edges of the shell 49 is permanently attached to the inside or back surface of the shell 49 where desired. This padding material 52 can also have uniform hole pattern 54 as necessary to provide and allow the necessary ventilation. This perforation pattern also distributes the impact energy on the front surface of the shell 49 to the user's leg or other areas of the body. As can be seen in FIG. 9, the guard 48 with its foam padding material 52 is preshaped or molded to have a partially curved configuration. The radius of this curvature is normally greater than the radius of curvature of the shinbone area of most users. It is desirable to have a large enough radius so that the guard will fit a person having an excessively large radius of curvature in the shinbone or leg area. The desirability of this configuration will be described below.

In this embodiment, as shown in FIG. 7, a pair of slots 56 are provided in the upper rounded portion of the shell 49. A single elongated slot 58 is provided near the lowermost portion of the shell 49. This slot is arranged transverse to the longitudinal axis of the shell 49 and can have a length of approximately 25 to 38 mm (1 to 1½"). A slidable rivet 60 is suitably anchored in the slot 58 and through a strap 60 which will allow the rivet to slide laterally in the slot 58 to allow positioning and movement between the strap 60 and the shell 49. Hook and loop type fasteners 64, 66, such as Velcro, can be used to adjust and hold the straps in place. As explained before the upwardly curved indentation 68 on the shell 49 is intended to provide a recess and clearance for foot movement which is necessary with a shin guard type protector.

As part of this invention it is to be understood that this same general type of structure can be used to form guards or shields which can be used for protection of various areas of the user's body, such as the thigh area of the leg, the forearm portion of the arm, the rib cage area, the shoulder area and any other vulnerable portion of the user's body. It is anticipated that these types of guards will be used for various activities and sports, such as cycling, moto-cross, skate boards, hockey, football, soccer, lacrosse, cricket and other contact sports.

In addition to the types of protection which have been described above, it is also possible that the guard of the present invention can be used to protect a pivotal body joint, such as the knee or elbow. As shown in FIG. 13 and 14, a guard 70 for protecting the elbow area of the user is provided which includes an upper shell section 72 and lower shell section 74. The upper and lower sections 72, 74 have a generally curved configuration which, as shown in FIG. 14, has an inside radius of curvature which is sufficient in a preliminary form to fit the largest bicep and forearm areas that are expected to be encountered. The upper and lower section 72, 74 are interconnected by a narrower linking or bridging section 76 which has interference relief formed by notches 78, 80. Elongated slots 82 are provided on each side of the upper section 72 as well as the lower section 74. Straps 84 can be threaded through the slots 82 as shown in FIG. 13 and the ends held by the conventional hook and loop type fastener to allow the guard 70 to be firmly held in place over the elbow of the user. It is also understood that the inside surface of the guard 70 can be lined with a foam padding material similar to that which was illustrated and described in conjunction with the previous embodiments.

As will be explained later the material from which the guard shell is fabricated is selected for its flexibility as well as its rigidity which allows the shell as described to flex in the linking or bridging section 76 which allows movement of the arm or leg and yet allows additional protection to the vulnerable area associated with the elbow or knee. The notch areas 78, 80 are provided on each side of the guard to allow sufficient clearance for the relative movement between the upper and lower sections without general contact between the adjacent edges of these sections. This allows additional protection, but still protects the lateral areas of these regions.

Up to this point, most of the guards or shields that have been shown and described are similar to the arrangements which have previously been provided to the general public. There is one major difference, however, in that the guards that have been described herein have been partially or generally shaped to fit or accommodate a relatively large individual or user. One of the primary purposes of the present invention is to provide a guard which can be custom fitted or molded to fit the exact contour, shape and size of each individual user. This is accomplished in the present invention by the use of a unique material which has been found to provide new and unusual results which heretofore have never been known or suggested for use in this type of protector. With the materials which the applicant has found for use in forming the shell it is a relatively easy and simple process to custom fit and mold the shell to fit the exact contour, shape and size of the intended wearer. When this is accomplished then the protection that is provided by the guard increases astronomically in that the impact energy to which the guard or shield is subjected is capable of distributing, coupling and transmitting this energy safely over a wider area. In this way, the energy is dissipated safely so as to eliminate tissue and skeletal damage and injury.

In order to provide this unique result, the applicant has found that materials produced from the Olefin family of long chain, synthetic polymers containing carbon produces a material which has a high impact resistance yet is relatively flexible and yet easily formed at relatively low temperatures. These materials are ethylene/-methacrylic acid based copolymers. This material is classified as ionomer resins which are thermal plastic polymers that are ionically cross linked. This latter material is produced by Dupont Company under the trademark "SURLYN" and "NUCREL". For the purpose of this invention the applicant has found that "SURLYN" ionomer resins are uniquely capable of providing the desired characteristics as well as the low temperature thermal forming characteristics that are required.

"SURLYN 9910" has been found to be quite satisfactory for this purpose. This product has a thermal forming temperature of between approximately 50°–80° C. (124°–178° F.). This allows the use of the hot water found in the common domestic hot water system having a temperature of approximately 60°–70° C. (140°–160° F.) temperature. This temperature range has been found to be quite satisfactory for softening the "SURLYN 9910" material to make it easily pliable and moldable. It is to be understood that any type of ionomer resin which meets the stated criteria for this purpose is considered to be satisfactory for this invention.

FIG. 10 illustrates the placement of a guard shell 90 according to the present invention under the hot water flow (W) of the conventional hot water tap or faucet (F). The shield is held under the hot water faucet (F) for a suitable length of time, such as 30 to 90 seconds, in order to allow the material of the shell 90 to absorb the heat and stabilize the temperature of the material across the entire shell 90. Once the temperature of the shell material has stabilized at the proper temperature the shell is immediately positioned at the proper location on the user's leg (L). If the shell 90 has the foam padding material, this material will not conduct heat and will insulate the heat from the shell 90 to protect the skin of the user so as to not cause any superficial burns. If the shell 90 does not have the foam padding material, a thin towel or other cloth can be positioned over the leg before applying the heated shell 90.

The guard shell is held tightly to the surface of the leg or body part for approximately 60 seconds while the guard cools below the freezing point of approximately 50° C. (124° F.) wherein the material regains its rigidity. As shown in FIG. 12, the shell is custom formed to fit the actual contours and shape of the user's leg or body part. In this way, a perfect custom fit is obtained by use of the method according to the present invention.

A complete guard or shield of this type which has been custom fitted to closely follow the contour of the user's leg, arm or other area is much more comfortable and eliminates many of the problems that are accustomed with this type of guard. In the past it has been found that ill fitting guards cause irritation, blisters and are generally uncomfortable to use during times of hazardous activity or quick movement. In addition, it is believed that a custom formed guard of this type will provide considerably better hazardous protection and prevent possible serious injury.

It is to be understood that any high impact semi-rigid formable material, such as "SURLYN" other ionomer resins or other materials that are included in the listed group have been found satisfactory for this intended purpose. It is mandatory that the material have a low forming temperature that is accessible from a hot water tap in order to eliminate the necessity for heat guns, high temperature radiators, boiling water and other special methods of applying heat that have been used in the past. With this characteristic, athletes and users of all ages can custom fit their guards without subjecting themselves to the hazards of burns and injuries which have been common place in the past.

While a custom fit body guard has been shown and described herein, this invention is not to be limited to the specific designs and illustrations which are contained herein, but it will be understood that variations and modifications of the invention can be effected within the spirit and scope of the invention.

What is claimed is:

1. An improved body guard to protect an area of the user's body during physical activity, the guard comprising:
   a) a shell means formed from thin sheet material, said shell means having a size and shape which substantially covers and closely fits the body area which is to be protected, said shell means being fabricated from an ionomer resin which has a high impact strength with flexibility at ambient temperatures and a thermal forming temperature within the range of 50°–80° C. whereby the user can apply heat to the member so as to raise the temperature of the member to the stated temperature range so that the member can be custom molded and fitted to the user's body area; and
   b) a holding means for holding the shell means firmly against the body area to be protected during said physical activity.

2. An improved body guard as defined in claim 1 wherein the holding means includes a sleeve having a strap means, said strap means being arranged to hold the holding means in position adjacent to the body area, said sleeve having a receptacle means which is arranged to receive and retain the shell means in position with respect to said body area.

3. An improved body guard as defined in claim 2 wherein said sleeve includes a padded layer of material which is positioned between the receptacle means and the body area to absorb impact energy applied to the shell means during physical activity.

4. An improved body guard as defined in claim 2 wherein said holder means is a strap means which has one or more continuous elastic bands that can be positioned to surround the body area and hold the sleeve and shell means in proper position.

5. An improved body guard as defined in claim 2 wherein said holding means is a strap means including at least two elongated flexible straps attached to said sleeve and including fastening means to adjustably hold said straps and sleeve in proper position.

6. An improved body guard as defined in claim 1 wherein said shell means has a layer of foam padding material permanently adhered to a surface of the shell means that is positioned against the body area whereby the member will be cushioned so that impact energy applied to said shell means will be absorbed and not directly transmitted to the user's body area.

7. An improved body guard as defined in claim 1 wherein the material of said shell means is formed from an ethylene/methacrylic acid based copolymer.

8. An improved body guard as defined in claim 1 wherein the material of said shell means is a "SURLYN" ionomer resin.

9. An improved guard to protect a movable joint area of a user's body, such as a knee or elbow body member during physical activity, the guard comprising:
   a) a shell means having a first and second section, said first and second sections being connected by a linking section which acts as a hinge means;
   b) said first and second sections of said shell means being arranged to extend along the body member on both sides of said body joint and being partially curved to generally fit the contour of said body member, a pair of notches being formed one on each side of said linking section to reduce the overall width of said linking section to allow relative movement between the first and second sections without interference during movement of the body joint;
   c) said shell means being fabricated from an ionomer resin having high impact strength while still flexible at ambient temperatures and having a thermal forming temperature within the range of 50°-80° C., said shell means being heated to a temperature within said range and closely held to the body member on either side of said joint while allowing the shell means to cool below the thermal forming temperature whereby it will take a permanent set so as to be custom fitted to the user's body; and
   d) a means for holding the shell means firmly against the body member after it has been custom fitted to protect the joint area during physical activity.

10. An improved guard for protecting a movable joint area as described in claim 9 wherein said holding means includes a plurality of straps attached to said first and second sections, said straps being arranged to be adjustably secured around the area of the body member adjacent to said movable joint area for holding the shell means in proper position.

11. An improved guard for protecting a movable joint area as defined in claim 9 wherein said first, second and linking sections of said shell means include a layer of foam padding material permanently adhered to a surface of said sections by suitable adhesive means whereby the foam padding material will be interspersed between the shell means and the joint area of the user to cushion impact energy applied to the shell means to prevent injury to the user.

12. An improved body guard for protecting a movable joint area as defined in claim 9 wherein the material of said shell means is formed from an ethylene/methacrylic acid based copolymer.

13. An improved guard to protect a movable joint area as defined in claim 9 wherein the material of said shell means is a "SURLYN" ionomer resin.

* * * * *